United States Patent [19]

Scott et al.

[11] Patent Number: 4,782,024

[45] Date of Patent: Nov. 1, 1988

[54] FERMENTATION PROCESS AND FERMENTER

[75] Inventors: Roger H. Scott, Hurworth-On-Tees, Nr. Darlington; Peter W. Dodd, Middlesbrough, both of England

[73] Assignee: Imperial Chemical Industries PLC, London, England

[21] Appl. No.: 925,556

[22] Filed: Oct. 31, 1986

[30] Foreign Application Priority Data

Nov. 6, 1985 [GB] United Kingdom ............... 8527335

[51] Int. Cl.⁴ ............................................ C12N 1/32
[52] U.S. Cl. .................................... 435/247; 435/243; 435/313; 435/314; 435/316; 435/818
[58] Field of Search ............... 435/299, 300, 301, 313, 435/314, 315, 316, 287, 247, 243, 253, 818

[56] References Cited

U.S. PATENT DOCUMENTS

| | | | |
|---|---|---|---|
| 3,910,826 | 10/1975 | Kataoka | 435/316 |
| 3,963,581 | 6/1976 | Giacobbe et al. | 435/316 |
| 3,982,998 | 9/1976 | Hitzman et al. | 435/315 |
| 4,036,699 | 7/1977 | Quigg | 435/316 |
| 4,048,017 | 9/1977 | Roesler | 435/247 |
| 4,204,042 | 5/1980 | Chelbe | 435/314 |
| 4,237,693 | 12/1980 | Maslen et al. | 60/648 |
| 4,302,542 | 11/1981 | Hitzman | 435/316 |
| 4,380,584 | 4/1983 | Hitzman | 435/314 |

FOREIGN PATENT DOCUMENTS

| | | |
|---|---|---|
| 80277 | 1/1983 | European Pat. Off. . |
| 1353008 | 7/1970 | United Kingdom . |
| 1346061 | 2/1974 | United Kingdom . |
| 1370892 | 10/1974 | United Kingdom . |
| 1417487 | 12/1975 | United Kingdom . |
| 1417486 | 12/1975 | United Kingdom . |
| 2108151 | 5/1983 | United Kingdom . |

Primary Examiner—James C. Yeung
Attorney, Agent, or Firm—Cushman, Darby & Cushman

[57] ABSTRACT

A "pressure-cycle" fermentation process and fermenter wherein an oxygen-enriched gas containing at least 30% by volume oxygen is supplied to the fermenter downcomer and the nutrient supply to the fermenter is such as to allow growth of the culture to continue in the downcomer. The process and fermenter may be used in the production of single cell protein using bacteria such as *Methylophilus methylotrophus* or yeasts such as *Fusarium graminearum* Schwabe.

8 Claims, 3 Drawing Sheets

FERMENTATION PROCESS AND FERMENTER

This invention relates to a fermentation process using a fermenter of the "Pressure Cycle" type and to an improved "Pressure Cycle" fermenter.

A "Pressure Cycle" fermenter is essentially a system for aerobic fermentations which comprises a chamber of ascending flow (riser) and a chamber of descending flow (downcomer) connected at their upper and lower ends to permit a culture to be circulated around the system. An oxygen-containing gas can be injected into the system at or near the lower end of the riser and this serves to aerate the culture and to cause it to circulate upwardly in the riser and downwardly in the downcomer. Most growth takes place in the riser and nutrients including the carbon source are usually added to culture in the riser. "Pressure Cycle" fermenters are very suitable for processes for the production of single cell protein (SCP) such as the processes disclosed in UK Pat. Nos. 1346061 and 1370892. In the "Pressure Cycle" fermenters disclosed in UK Pat. Nos. 1353008 and 1417487 there is provision for injecting an oxygen-containing gas into culture in the downcomer.

In conventional processes for the production of SCP using "Pressure Cycle" fermenters the productivity of the process can sometimes be reduced due to oxygen-deficient growth of culture taking place in the downcomer. Oxygen-deficient growth occurs more often when the microorganism being cultured is a yeast rather than a bacterium due mainly to viscosity effects and in the case of a yeast can lead to the production of ethanol.

According to the present invention we provide a process for the aerobic fermentation of a culture containing microorganisms in which the culture is continuously circulated around a system having a riser and a downcomer communicating with each other at their upper and lower ends, oxygen-containing gas being supplied to culture in the lower part of the riser and in the downcomer in amounts sufficient for the culture, i.e. the amounts being matched to the needs of microorganisms in the culture, and to circulate it around the system and nutrients including a carbon source being supplied to culture in the riser characterised in that the oxygen-containing gas supplied to the downcomer contains at least 30% by volume of oxygen and is supplied in an amount within the range 0.2% to 20% by volume of the amount of oxygen-containing gas which is supplied to the riser and sufficient nutrients including the carbon source are supplied to culture in the downcomer or are carried by the circulating culture into the downcomer to permit growth of culture to occur in the downcomer.

Further according to the invention we provide a fermenter which comprises a riser and a downcomer communicating with each other at their upper and lower ends, riser-gas supplying means for supplying oxygen-containing gas to the lower part of the riser sufficient to aerate and circulate a culture contained in the fermenter, downcomer-gas supplying means for supplying gas to the downcomer, and nutrient-supplying means for supplying nutrients including a carbon source to culture in the riser characterised in that the downcomer-gas supplying means is such that it can supply a gas containing at least 30% by volume of oxygen in an amount within the range 0.2% to 20% by volume of the gas supplied to the riser by the riser-gas supplying means and the nutrient-supplying means is such that it can supply nutrients including the carbon source to culture in the riser or in the riser and the downcomer in a manner such that nutrients are available to culture in the downcomer in an amount sufficient to permit growth of the culture to occur in the downcomer.

The gas supplied to the downcomer in the process of the invention may be oxygen or any mixture of a gas or gases inert in terms of the fermentation and oxygen which contains at least 30% oxygen by volume. Preferably the downcomer gas is oxygen-enriched air containing at least 30% oxygen by volume, the additional oxygen being provided from any suitable source. The gas supplied to the riser may be oxygen, air or any mixture of a gas or gases inert to the fermentation and oxygen which can provide sufficient oxygen adequately to aerate the culture in the riser. Preferably the riser gas is air.

Oxygen-containing gas may be supplied to the riser and the downcomer by any suitable means. Conveniently gas is supplied to the risrr through a perforated pipe located at its bottom end which provides a plurality of nozzles. A perforated pipe may also be used to supply gas to the downcomer. However it is also possible to supply gas to the downcomer using more complicated spargers such as venturi nozzles, porous media, open ended pipes with associated downstream bubble break up meshes, grids, vanes or moving parts, side stream addition using some additional motive forces which would be wholly or in part the downcomer gas itself or any combination of these techniques.

The main supply of gas to the downcomer is preferably made to the upper half thereof. In some situations it may be desirable to make a further addition of gas to the lower half of the downcomer but this will usually be an auxilliary addition of a lesser amount of gas than is added to the upper half. In particular it is preferred that the main addition of downcomer gas is made in the region between 10% to 40% of the length of the downcomer from the top thereof. In a tall fermenter it may be desirable to make more than two additions of gas to the downcomer, for example in a downcomer of height 40 meters five additions may be made.

The process of the invention is suitably used to produce single cell protein (SCP), microorganisms being grown in a culture containing an appropriate carbon source. Any suitable microorganisms may be grown, including yeasts and bacteria, and a wide range of carbon sources may be used for example carbohydrates, hydrocarbons and oxygenated hydrocarbons such as alcohols. An example of a process in which bacteria are grown is the process disclosed in UK Specification No. 1370892. In this process strains of the species *Methylophilus methylotrophus* (formerly known as *Pseudomonas methylotropha*) are grown in a culture containing methanol as a carbon source. Cultures of suitable strains of *Methylophilus methylotrophus* have been deposited at three culture collections with the following corresponding accession numbers at the different collections:

1. National Collection of Industrial Bacteria (NCIB), Torrey Research Station, Aberdeen, Scotland, UK - NCIB Nos. 10508 to 10515 and 10592 to 10596;

2. Agricultural Research Culture Collection (NRRL), Peoria, Ill., USA - NRRL Nos. B 5352 to 5364;

3. Fermentation Research Institute, Agency of Industrial Science and Technology, Japan - FERM 1215 to FERM 1227. An example of a process in which yeasts are grown is the process disclosed in UK Specification No. 1346061. In this process strains of *Fusarium*

*graminearum* Schwabe are grown in a culture containing glucose as a carbon source. A culture of a suitable strain of *Fusarium graminearum* Schwabe has been deposited at the Commonwealth Mycological Institute, Kew, Surrey, England with the accession number IMI 145425. A number of variants of IMI 145425 have also been deposited at the Commonwealth Mycological Institute and have the accession numbers IMI 154209 to IMI 154213.

The fermenter of the invention is suitably a modification of the basic fermenters disclosed in UK Specification Nos. 1353008, 1417486, 1417487 and 2002417 having appropriate arrangements for admitting gas to the downcomer and nutrients including the carbon source to the riser or to the riser and the downcomer. Nutrients are supplied to culture in the fermenter in a manner such as to permit growth of the culture to occur in the downcomer.

An important advantage of the invention when used in a process for the production of SCP is that it enables a significant improvement in the productivity of the SCP production process to be achieved. The reasons for this improvement in productivity include:

1. The addition of oxygen to the downcomer enables the dissolved oxygen tension (DOT) profile therein to be improved so that supplies of a carbon source added to culture in the downcomer or carried over into the downcomer can be used in a more uniform manner by microorganisms in the culture for growth; and 2. The oxygen added to the downcomer facilitates the maintenance of minimum DOT requirements throughout the fermenter cycle. Preferably the DOT at the bottom of the downcomer is maintained above 10 mm Hg.

The invention is illustrated by the accompanying drawings wherein.

Figure 1:
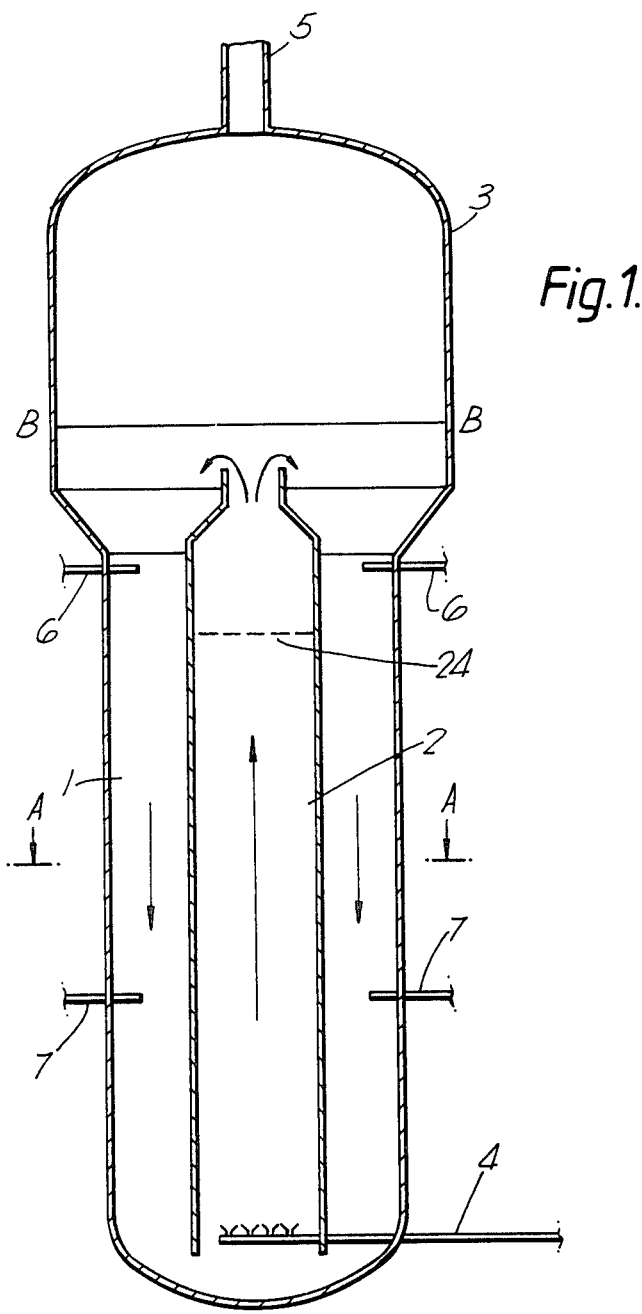
FIG. 1 is a side elevation of one embodiment of the fermenter according to the invention.
Figure 2:
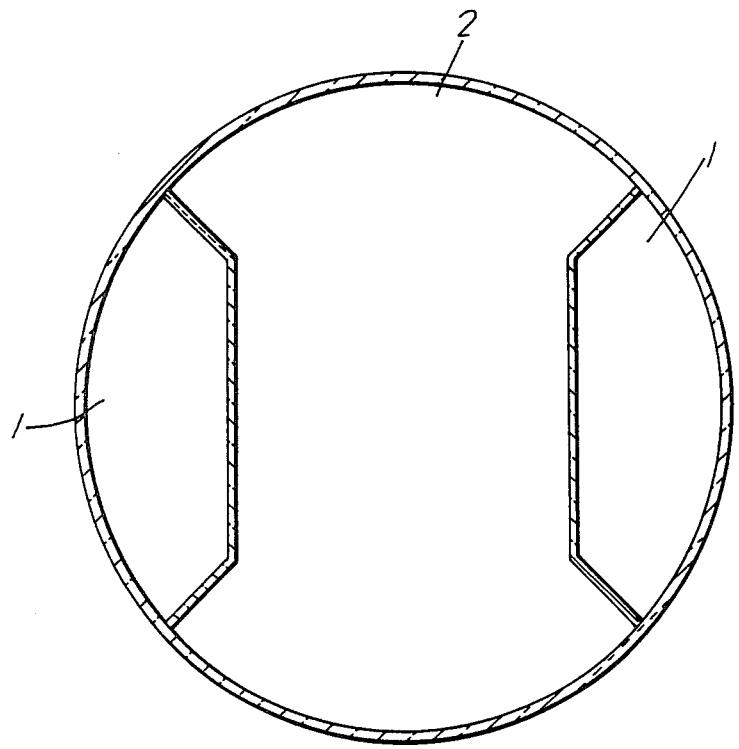
FIG. 2 is a cross-section along the line A—A of FIG. 1.
Figure 3:
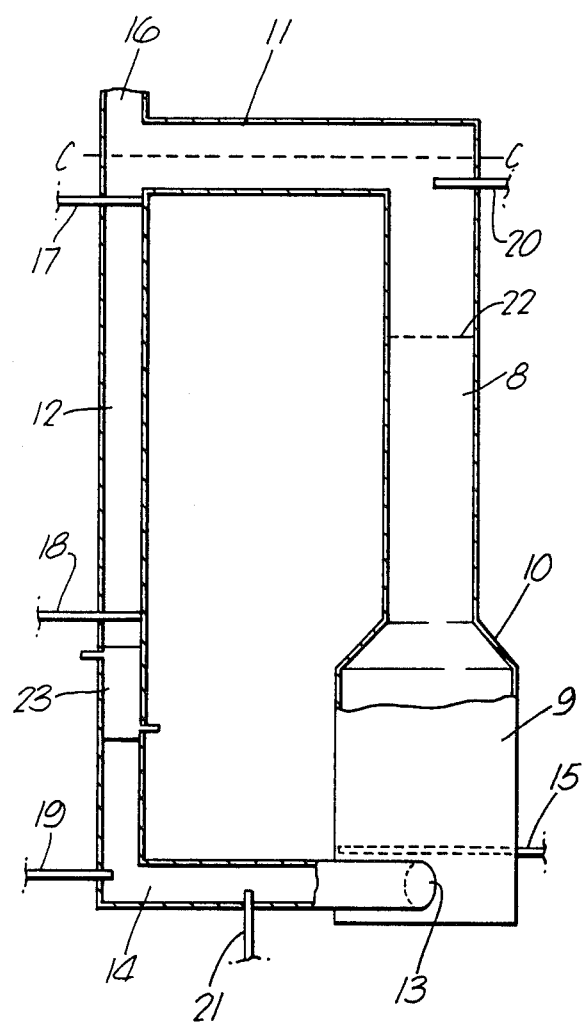

FIG. 3 is a side elevation of a second embodiment of the fermenter according to the invention. The fermenter shown in FIGS. 1 and 2 has an outer shell which comprises two cylindrical sections of different cross-sectional area surmounted by a dome, the cross-sectional area of the upper of the two sections being greater than that of the lower. The lower section is divided by a pair of partitions parallel to its axis into a riser 2 and a downcomer 1, the downcomer being effectively divided into two zones. The upper section and the dome enclose a compartment 3. Air is injected into the lower part of riser 2 through sparger 4 and oxygen or oxygen-enriched air is injected into the two zones of downcomer 1 through upper pipes 6 and lower pipes 7. Gas is disengaged from the liquid in the fermenter in the upper parts of riser 2 and downcomer 1, passing through liquid surface B . . . B into the gas-filled part of compartment 3 from whence it leaves the fermenter through port 5. Nutrients are added to the culture in the fermenter through pipes not shown in FIGS. 1 and 2. Nutrients including the carbon source are either added to the culture in both the riser and the downcomer or into culture in the riser only in amounts sufficient for nutrients to be carried over into the downcomer to enable growth of the culture to continue in the downcomer. Preferably the carbon source is added to culture in the riser through a large number of holes in a network of pipes as described in UK Patent Specification No. 1523583. Riser 2 also contains a series of baffles such as 24. The two zones of downcomer 2 may contain heat exchangers (not shown in the drawings).

The fermenter shown in FIG. 3 has a riser comprising cylindrical upper and lower sections 8 and 9 respectively connected through a reducing piece 10, upper section 8 having a smaller diameter than lower section 9. The upper section 8 of the riser is connected through upper connecting piece 11 to the upper end of cylindrical downcomer 12. Lower section 9 of the riser is connected at 13 with lower connecting piece 14 which connects it with the base of downcomer 12. Air is sparged into the lower section 9 of the riser through sparge pipe 15 causing continuous circulation of a culture which occupies the fermenter up to the level C—C. Upper connecting piece 11 is not allowed to run full of liquid in order to allow a free surface from which gases such as air and carbon dioxide escape from the medium and pass out through port 16. Oxygen or oxygen-enriched air is sparged into downcomer 12 through upper pipe 17 and lower pipe 18, upper pipe 17 being the main supply with lower pipe 18 being an auxilliary supply source.

Nutrients including the carbon source are added to culture in the riser and the downcomer or to culture in the riser alone in which case the nutrients are added in amounts such that they are carried over into the downcomer so that growth of the culture can continue there. Nutrients may be added through pipes 19 and 21. Preferably the carbon source is added to the culture in the riser through a large number of holes in a network of pipes as described in UK Patent Specification No. 1523583. Product is removed from the fermenter through pipe 20. The upper section 8 of the riser contains a series of baffles such as 22. Downcomer 12 contains a heat exchanger 23.

When the process of the invention is operated to produce single cell protein by growing cells of a *Methylophilus methylotrophus* strain in a culture containing methanol as a carbon source, operation of the process to produce a well designed DOT profile around the fermenter results in polysaccharide production being considerably reduced. When the process is used to grow *Fusarium graminearum* Schwabe on a glucose-containing culture a well designed DOT profile leads to a reduction in ethanol production.

For example a culture of *Fusarium graminearum* Schwabe growing in the fermenter of FIG. 3 having a nominal volume of 50 m$^3$ which is not supplied with oxygen-enriched gas in the downcomer will produce approximately 1 g/l of ethanol when the cell concentration is approximately 10 g/l. When the process is operated in accordance with the invention and oxygen is injected into the culture in the upper half of the downcomer the ethanol content falls to approximately 0.01 g/l for a similar concentration. The optimum position for injecting the oxygen in any particular case can be determined by computer calculation.

We claim:

1. A process for the aerobic fermentation of a culture containing microorganisms in which the culture is continuously circulated around a system having a riser and a downcomer communicating with each other at their upper and lower ends, oxygen-containing gas being supplied to culture in the lower part of the riser and in the downcomer in amounts sufficient for the culture and to circulate it around the system and nutrients including a carbon source being supplied to culture in the riser wherein the oxygen-containing gas supplied to the downcomer contains at least 30% by volume of oxygen and is supplied in an amount within the range 0.2% to 20% by volume of the amount of oxygen-containing gas which is supplied to the riser and sufficient nutrients including the carbon source are supplied to culture in the downcomer or are carried by the circulating culture into the downcomer to permit growth of culture to occur in the downcomer.

2. A process according to claim 1 wherein the oxygen-containing gas supplied to the downcomer is supplied to the upper half thereof.

3. A process according to claim 2 wherein the oxygen-containing gas is supplied in a region between 10% and 40% of the length of the downcomer from the top thereof.

4. A process according to claim 1 which forms a step in a process for the production of single cell protein.

5. A process according to claim 4 wherein the microorganism is a bacterium belonging to the species *Methylophilus methylotrophus* and the culture contains methanol as a carbon source.

6. A process according to claim 4 wherein the microorganism is a yeast belonging to the species *Fusarium graminearum* Schwabe and the culture contains glucose as a carbon source.

7. A process according to claim 1 wherein the amount of oxygen in the gas added to the downcomer is sufficient to maintain the dissolved oxygen tension (DOT) in the culture at the bottom of the downcomer at a value above 10 mm Hg.

8. A fermenter which comprises a riser and a downcomer communicating with each other at their upper and lower ends, riser-gas supplying means for supplying oxygen-containing gas to the lower part of the riser sufficient to aerate and circulate a culture contained in the fermenter, downcomer-gas supplying means for supplying gas to the downcomer, and nutrient-supplying means for supplying nutrients including a carbon source to culture in the riser characterised in that the downcomer-gas supplying means is such that it can supply a gas containing at least 30% by volume of oxygen in an amount within the range 0.2% to 20% by volume of the gas supplied to the riser by the riser-gas supplying means and the nutrient-supplying means is such that it can supply nutrients including the carbon source to culture in the riser or in the riser and the downcomer in a manner such that nutrients are available to culture in the downcomer in an amount sufficient to permit growth of the culture to occur in the downcomer.

* * * * *